United States Patent [19]

Lasky

[11] Patent Number: 4,759,045
[45] Date of Patent: Jul. 19, 1988

[54] QUALITY TEST STANDARD FOR X-RAY MAMMOGRAMS

[76] Inventor: Harold J. Lasky, 716 Roslyn Pl., Evanston, Ill. 60201

[21] Appl. No.: 916,162

[22] Filed: Oct. 7, 1986

[51] Int. Cl.⁴ .............................................. A61B 6/04
[52] U.S. Cl. .................................... 378/37; 378/162; 378/207
[58] Field of Search .................. 378/18, 37, 162, 165, 378/204, 207, 210; 250/252.1

[56] References Cited

U.S. PATENT DOCUMENTS

| 2,439,374 | 4/1948 | Leader et al. | 378/165 |
| 3,578,971 | 5/1971 | Lasky | 378/37 |
| 4,506,676 | 3/1985 | Duska | 378/162 |

FOREIGN PATENT DOCUMENTS 3045186  9/1981  Fed. Rep. of Germany ...... 378/204

OTHER PUBLICATIONS

"Roentgenography of the Breast" by Kremins American Jour. of Roentgenology & Nuclear Medicine, vol. 80, #6, Dec. 1958.

Primary Examiner—Craig E. Church
Assistant Examiner—John C. Freeman
Attorney, Agent, or Firm—Michael G. Berkman

[57] ABSTRACT

A method and apparatus for simply, rapidly and reliably determining the diagnostically relevant quality and the general reliability of X-ray mammograms. A mammogram quality reference test standard is provided in which particulate matter of selectable form, composition and size is temporarily affixed on the breast itself for exposure to radiation during production of a diagnostic mammographic radiograph. In a preferred embodiment of the invention, the test standard utilizes particulate matter which includes smaller particles useful in evaluating resolution in the film as well as contrast, and larger particles useful primarily in evaluating contrast in the film. The test zone itself is clearly delineated by suitable, easily visible markers so as clearly to be identifiable, and the area occupied by the test standard is preferably kept small so as to ensure a minimum of interference with a viewing of the image of the tissues of the breast.

21 Claims, 1 Drawing Sheet

QUALITY TEST STANDARD FOR X-RAY MAMMOGRAMS

FIELD OF THE INVENTION

This invention relates to a method and to a test standard for assessing the quality and the reliability of a radiographic image produced in a radiological medical procedure. More particularly, the invention is directed to a test tab for use during a diagnostic X-ray examination to provide in a mammographic radiograph reference images the visual appearance of which in the image itself provides information indicative of the quality of the mammogram produced in a diagnostic mammographic procedure.

BACKGROUND OF THE INVENTION

The apparatus used and the methods employed in the radiographic examination of the breast are well known in the art. A preferred technique and apparatus are described in H. J. Lasky U.S. Pat. No. 3,578,971, and the entire disclosure of that patent is hereby incorporated herein by reference, to the extent it is not inconsistent herewith.

The present invention finds special utility as a test standard providing, in mammograms, visual indicia for quickly and effectively judging the quality of mammograms.

It has become an established and wide-spread medical practice to conduct such X-ray tests on female subjects to determine whether any of the subjects suffers from breast cancer or whether any of the radiologically-examined tissues evidences other abnormal conditions. Since the examinations themselves are carried out by different medical practitioners and by X-ray technicians using various different types of X-ray equipment and recording media, there has been a real problem in establishing the extent to which the X-ray pictures produced would be expected reliably to show the true condition of the tissue examined. The problem described is aggravated by the fact that many different "reviewers" may be involved in the overall investigation.

Breast phantoms which are designed to "simulate" the breast have been used to test the capability of the X-ray system, with respect to resolution and contrast. However, this approach has not proven widely applicable, is costly and not widely accepted.

It has become undeniably evident that it is exceedingly difficult, relying on visual examination of a given X-ray image, and nothing more, to know with any degree of certainty whether the image represents a high-quality and, accordingly, a reliable visual representation of the existing field or, whether the plate is of such caliber as not to merit unquestioned reliance. If the image quality is inadequate to demonstrate tiny particles of calcium, often the only sign of an early cancer, the interpreter would not know that they were present. A third party X-ray expert or trained radiologist independently examining the plate would not have an objective awareness or perspective as to the technical deficiency of the radiograph itself.

While the type of problem indicated may not exist in those instances in which a tumor or cancerous tissue is well developed and, thus, clearly visible to all, one will appreciate that in the very early stages of the development of such tissue abnormalities, a reliable diagnosis based upon an examination of X-ray plates is much more difficult. Yet early diagnosis is a very important element in arresting and in effectively treating cancerous tissues and tissues which exhibit conditions precursory to cancer, particularly breast cancer.

It is, accordingly, the aim of the present invention to overcome the inadequacies and the shortcomings of prior techniques and devices and to provide a simple and effective apparatus and method by which a person examining a mammographic X-ray film or plate may reliably know, from a visual examination of the developed mammogram itself, the "quality" of the developed image and, accordingly, the extent to which the radiograph may be relied upon to indicate the absence of, or, conversely, to show the presence of "abnormal" findings.

SUMMARY OF THE INVENTION

The present invention comprises a quality test standard for radiographic mammograms. The standard itself is incorporated in to establish or to provide in the developed X-ray picture a well-defined and identifiable reference field or zone. Visual indicia in this reference zone may conveniently be compared with references as the latter are known to appear on a high-quality X-ray film or plate. Thus, one may judge from a viewing of the specially-produced reference zone on the X-ray mammogram the exposure conditions under which the image was generated and the quality and the reliability of the radiograph under examination.

In a preferred embodiment of the invention there is provided a special tab, disc, or "label" which is physically affixed to the breast tissue to overlie the tissue during the actual taking of the X-ray mammograph. Conveniently the tab attached to the tissue includes particles, preferably distributed as a unilayer coating, carried by an X-ray transparent sheet or band. The particles themselves are opaque to X-rays and are of specific, selectable compositions and preferably in particular size ranges. The visual appearance of the solid particles, as they are seen on the developed radiograph provides a reliable indication of the resolution and of the contrast in the mammogram.

Through extended and careful investigative research conducted during development of the present invention, the selection of particular "solids" has made it feasible to produce in the X-ray visual or indicia which simulate or which at least parallel or are comparable to X-ray images produced by typical abnormal tissues, including images of tissues as they appear in an early stage of such abnormal growths or developments.

For example, in accordance with the method and apparatus of the present invention, the visual evidence of particular test particles in the developed X-ray simulates, in an image which has in fact been properly exposed and processed, the appearance of tiny particles of calcium such as may occur in the breast. Such perceived appearances constitute one of the X-ray signs of cancer conventionally "looked for" in mammograms. The faithful and proper appearance of these calcium-simulating particles in the reference test zone of the mammogram provides objective and concrete assurance that the exposure and processing parameters and the quality of the film meet predetermined established reliability criteria. Conformance of the images of the particles in the delineated test area to similarly generated reference images as they appear in mammograms of medically-confirmed quality and reliability demonstrates that the mammogram is of a quality to justify reliance on the radiograph as a proper basis for a meaningful clinical diagnosis.

A principal object of the invention is to provide a simple apparatus and method for use in conjunction with diagnostic X-ray mammography to provide an indication of the quality and the reliability of a mammogram produced in a radiological examination of breast tissue.

A related aim of the invention is to provide in a diagnostic radiographic X-ray mammogram a visually perceptible reference zone an examination of which will immediately apprise a reader of the X-ray of the quality and reliability of the film.

Yet another object of the invention is to provide a quality test standard which will produce, in a medical radiographic test image, a readily identifiable reference test zone, a visually perceptible appearance of which will be indicative of the quality of the film as characterized by resolution and contrast parameters.

It is an important object of the invention to provide an X-ray film quality test, tab-like device for support on the breast tissue during X-ray exposure in a diagnostic mammographic procedure.

In a preferred embodiment of the invention there is provided a test tab which carries particulate test material of a composition and of a particle size such that in a mammogram generated, the test material provides an appearance simulating tiny particles of calcium, as such particles may appear had they occurred in the tissue of the breast itself, the visual perceptibility of the image of the test material serving to indicate achievement of adequate resolution in the generated film.

A feature of the test standard of the invention is that it includes particulate matter which, in the radiograph generated, will provide a reliable visual indication of both the resolution and the contrast qualities achieved in a medical X-ray mammogram.

In a preferred embodiment of the test standard of the invention, particles of two different compositions and in two different sizes are included as reference materials for film quality evaluation, including evaluation of the resolution and of the contrast parameters of the film.

It is an object of the present invention to provide in a diagnostic mammogram an image-quality-indicating test zone which is clearly identified and delineated in the radiograph and in which the overall area is sufficiently small so as to ensure minimal interference with interpretive viewing and evaluation of the mammogram itself.

It is a feature of the quality test standard of the present invention that there are provided a method and apparatus for use during a procedure for producing an X-ray mammogram for enabling a reader of the radiograph to discern immediately the quality and the reliability of the image as a diagnostic tool.

Other and further objects, features and advantages of the invention will become apparent from a consideration of the following specification taken in conjunction with the drawings.

DESCRIPTION OF ILLUSTRATED EMBODIMENT

The aims and objects of the invention are realized through the use of a simple device which is useful as a test standard for providing visual evidence indicative of the quality and of the reliability of a mammogram produced in carrying out a radiographic examination of the human breast. In a preferred embodiment of the invention there is provided a radiograph quality reference test standard which includes particulate matter of selectable size, form and chemical composition. The particulate matter is positioned physically to overlie the breast tissue and is exposed radiographically during the exposure of the breast itself in producing a mammogram. The images of the particulate matter which are formed on the exposed and developed radiograph serve visually to indicate the quality of the image with respect to such important parameters as resolution and contrast.

In one preferred embodiment of the invention the particulate matter includes particles of two different ranges of sizes and each of a different composition. The smaller particles are viewed as an indication of the resolution quality of the film, as well as contrast. The larger particles are viewed more as an indication of the contrast achieved in the film.

Preferably, the smaller particles simulate, in the film generated, the appearance of tiny particles of calcium of the type which may occur in the breast and which are recognized as one of the X-ray signs of cancer for which one looks in a reading of mammograms.

It is within the concept of the invention to use test particles in a single size range only.

As an aid to locating and identifying the test zone viewing area in the mammogram itself and to distinguish that area from the breast structures, per se, the quality test standard of the invention includes a perimetric frame which circumscribes and delineates, on the mammogram, the viewing field which constitutes the reference test zone. The total area of the test zone is arbitrary, but is preferably kept small (in the order of 4 millimeters in diameter) in order to interfere only minimally with a viewing of the tissues of the breast.

Figure 1:
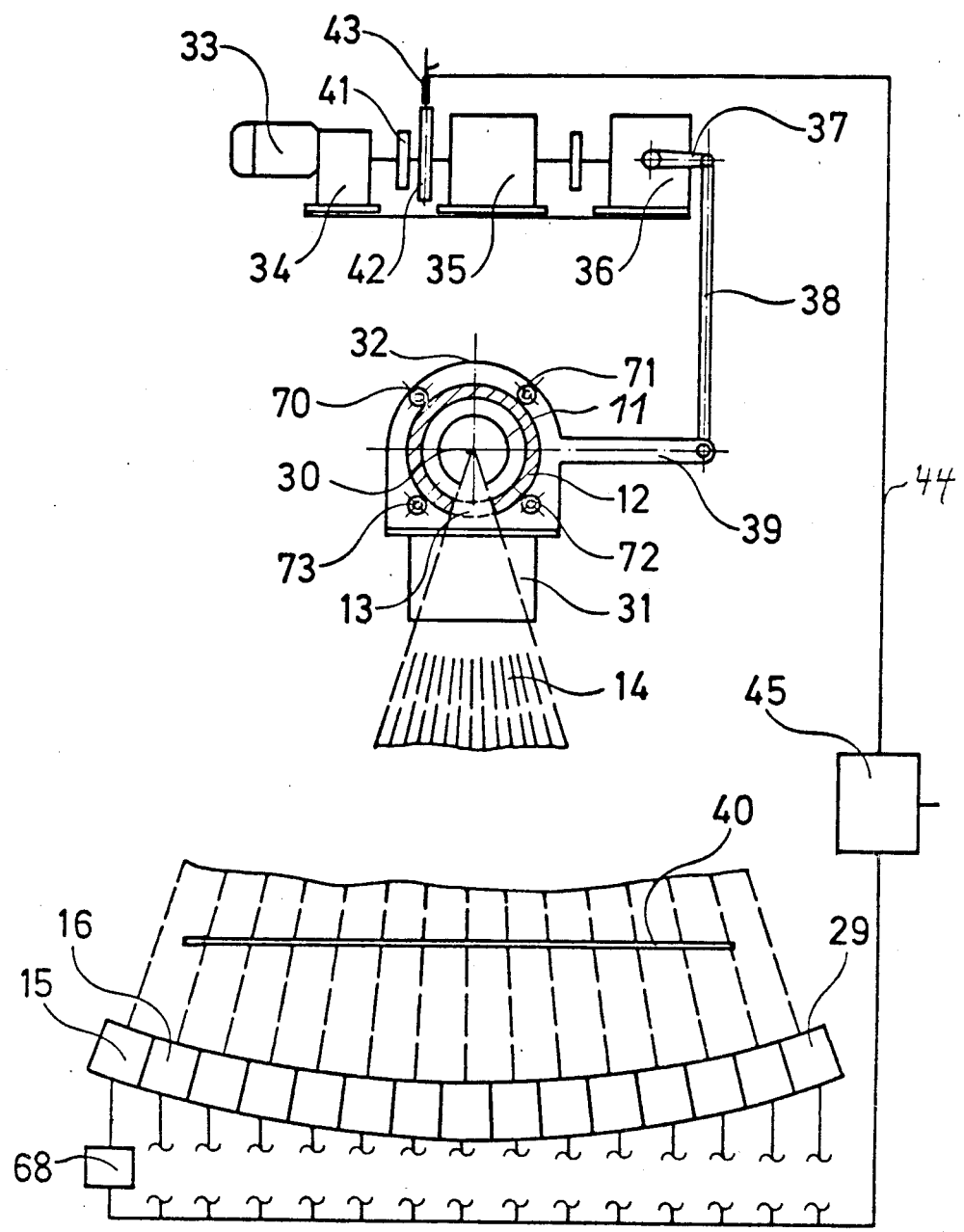
FIG. 1 is a top plan view of a test standard for use in X-ray mammography, and showing a test tab with its test particles and a demarking frame, according to the invention.
Figure 2:
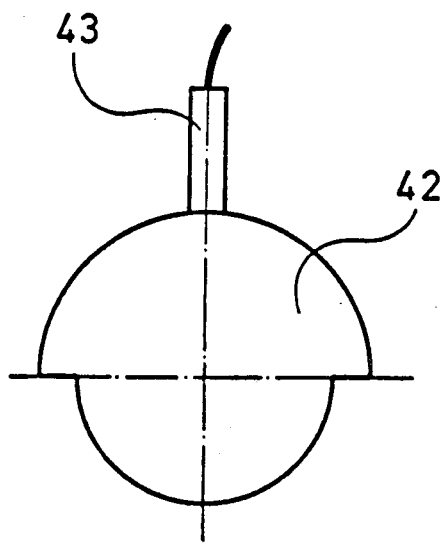
FIG. 2 is an enlarged, fragmentary, schematic representation of the test particles of the quality test standard of a preferred embodiment of the invention showing particles of two different sizes and general physical configurations.
Figure 3:
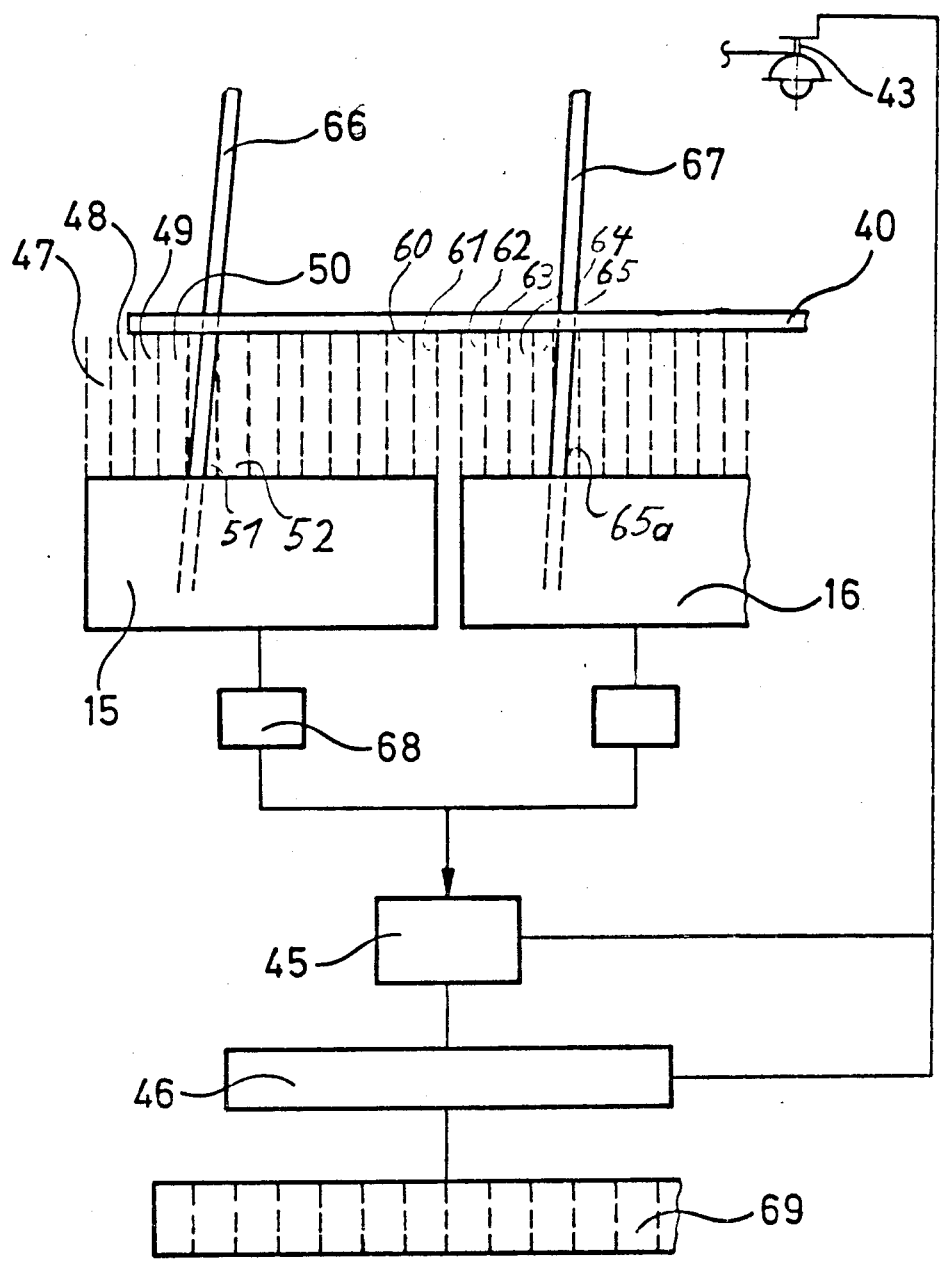
FIG. 3 is a perspective view of the component elements of the quality test standard of the invention of FIG. 1, shown in separate positions.

Referring more particularly to the drawings, there is shown in FIGS. 1 and 3, for the purpose of illustrative disclosure, and not in any limiting sense, a preferred embodiment of the device which constitutes the quality test standard 10 of the invention. In the illustrative embodiment shown, the quality test standard 10 includes a lower sheet 14 and an overlying upper sheet 16 each preferably of any fabric, web or light-weight plastic carrier material. The material itself may be clear, visually transparent, or otherwise, but in all cases transparent to X-rays. Suitable as plastic carriers are polyethylene, polypropylene, polyester film, and cellulose-derived sheet and ribbon. This list is in no sense limiting.

Interposed between the sheets 14 and 16 is particulate matter 20 in the physical form of distinct or discrete particles which preferably include smaller particles 24 and larger particles 26. The particles 20 are shown as distributed as a mono-layer and are confined between the enveloping or sandwiching carrier sheets 14 and 16. In one embodiment of the invention an auxiliary adhesive may be employed as an aid in ensuring that the particles 20 remain fixed or immobilized in position between the enveloping sheets 14 and 16 to maintain separation and individual integrity. In one preferred embodiment of the invention one (or both) of the particle-sandwiching sheets 14 and 16 may include a pre-applied pressure-sensitive adhesive coating 30. Such pre-coated sheet and ribbon-like products are well known, a commercial series of suitable products being widely marketed by the 3M Corporation under the trademark "Scotch Tape".

The particulate material 20 useful in the practice of the invention includes minerals, chemical compounds of various types (salts, etc.) which exhibit lesser and greater degrees of opacity to X-ray energy emanations. Preferably, the particles 20 include smaller particles 24 which serve to provide a visual indication of both the resolution and the contrast achieved in the mammographic film, and larger particles 26 providing images from which, primarily, the contrast achieved in the film may be discerned. As the smaller particles 24, the compound, zinc telluride, has proven to be especially useful, and as the larger particles 26, rock salt has the requisite parameters. These materials are not identified in a limiting sense. Other compounds and materials find utility in the practice of the invention.

Zinc telluride particles having a nominal diameter in the range of 0.1 to 0.2 millimeter are especially useful in that they produce, in the ultimate mammogram, perceptible images which simulate images caused by tiny particles of calcium of the type which may occur in the breast and which are recognized as one of the X-ray signs for which one looks in the diagnostic reading of mammograms.

The larger particles, of rock salt, or radiologically equivalent material, are conveniently of a nominal size in the range of 0.4-0.5 millimeter, it being understood that this size range is not critical. Based upon the teachings of the present invention, it will be possible for those skilled in the art to select other preferred compositions as well as other preferred size ranges for both the smaller 24 and the larger 26 particles. Such selection may, in the light of the present teaching, be made without exercise of the inventive faculty.

Figure 4:
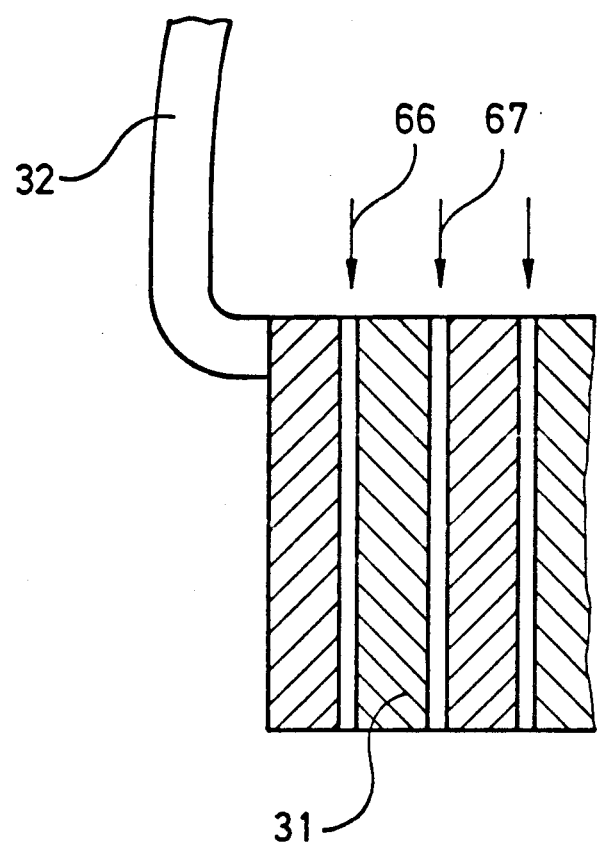
FIG. 4 is an enlarged, vertical cross-sectional view taken substantially on the lines 4—4 of FIG. 1.

Referring further to the drawing, and more particularly to FIGS. 1 and 4, in order clearly to identify and to delineate the areal zone in which the "test particles" 20 are to be viewed in the mammogram and clearly to distinguish this zonal test area and the standard itself from the remainder of the tissue area depicted in the mammogram, there are provided framing elements 40, opaque to X-rays, and arranged perimetrically about to delineate and to distinguish the field (film quality evaluation field) occupied by the test particles 20. Thin wires or strands 42 such as fine copper wires have been found useful and convenient for this purpose. The wires 40 are preferably bonded or adhesively secured in place to frame the test particles 20. Other kinds of metallic wires or mineral fibers may be used, providing that the framing elements are essentially opaque to X-rays. The physical arrangement or pattern in which the particles are retained may in itself provide a basis for identification of the test zone.

The test particles 20 carried between the sandwiching sheets 14 and 16 may be fastened in place on the surface 50 of the breast tissue (indicated schematically in FIG. 1) by means of adhesive applied to an underside of the lower sheet 14. Alternatively, a tape 56 coated with pressure-sensitive adhesive may be used to bond the quality test standard 10 in place.

The overall size of the test standard is such as to obviate interference in viewing of the breast tissue itself. Conveniently, the area occupied by the test assembly is equivalent to that of a circle having a diameter of about 4.0 millimeters. Again, this preferred area is not limiting.

While specific illustrative embodiments of the method and apparatus of the present invention, for achieving the purposes thereof, have been disclosed in the foregoing specifications, it will be understood that various modifications within the scope of the invention may occur to those skilled in the art. It is intended, therefore, that all such adaptations and modifications should be comprehended within the meaning and the range of equivalents of the disclosed techniques, compositions, and apparatus. Moreover, it is intended that all matter contained in the foregoing description or shown in the accompanying drawings shall be interpreted as illustrative and as not presented in any limiting sense.

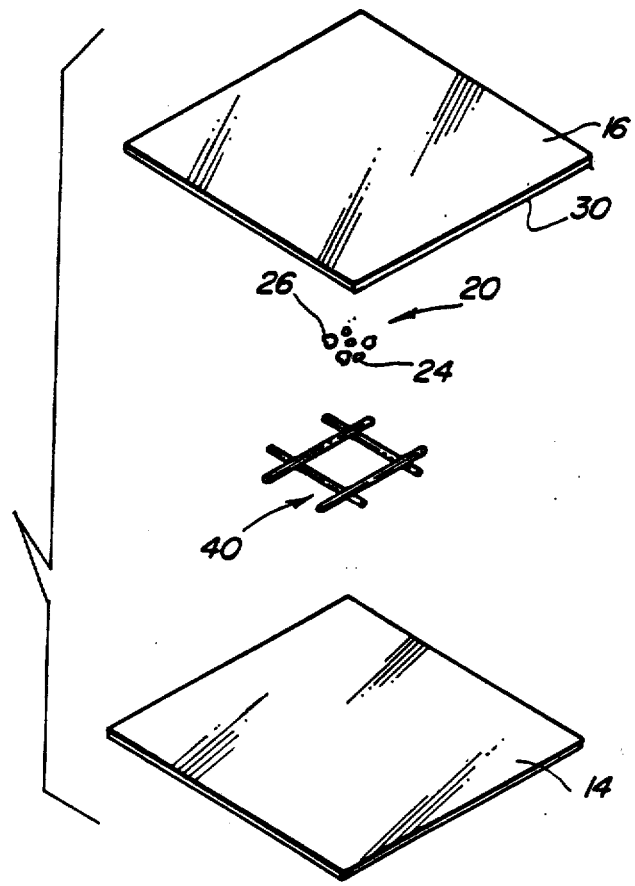

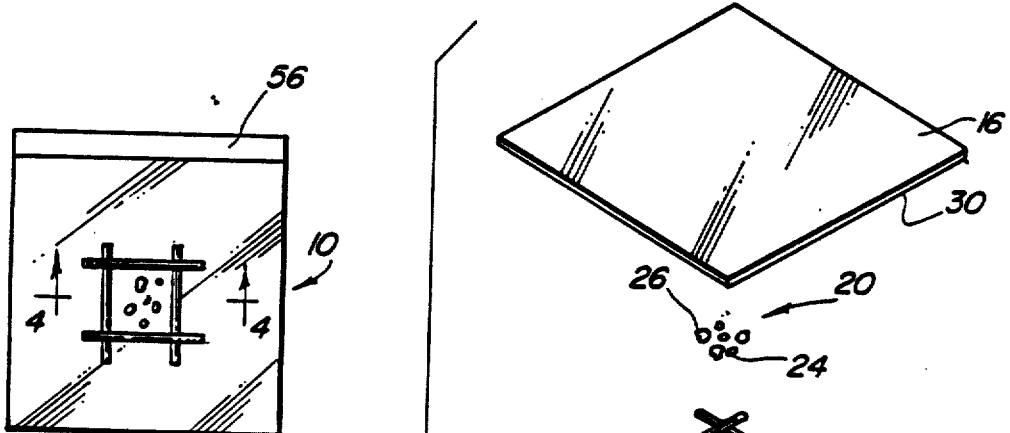
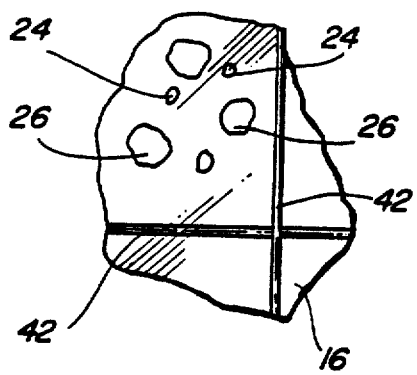
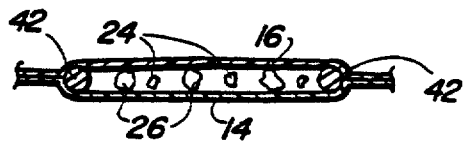

What is claimed is:

1. A method for a determining the reliability of and the reading quality of a radiographic medium produced in carrying out a diagnostic mammographic procedure, said method including the steps of positioning a test-material-carrying tab to overlie breast tissue in a path of a radiation source to be directed onto the tissue to be examined for producing a radiation-derived image on a mammographic medium, wherein said test-material is composed of particles whose X-ray image is used for determining the quality of the radiographic medium, activating an X-ray emanating source to generate a beam of radiant energy, directing the beam of radiant energy to impinge on the tissue-carried tab, on the test material of the tab, on the tissue to be examined, and on radiation-sensitive radiographic recording medium, simultaneously exposing the test material, the tissue and the recording medium to the radiant energy for generating a latent image of the irradiated tissue and of the irradiated test material of the tab, and processing the exposed radiographic recording medium to provide a visually perceptible image indicative of irradiation impedance characteristics of the tissue in an areal field of exposure of the tissue and simultaneously to provide a qualitative radiological visual reference representation of the test material of the tab, so as to establish objective and reliable indicia of the quality of a mammogram derived from a diagnostic mammographic procedure carried out.

2. A method for a determining the reliability of and the reading quality of a radiographic medium produced in carrying out a diagnostic mammographic procedure, said method including the steps of positioning a test-material-carrying tab to overlie breast tissue in a path of a radiation source to be directed onto the tissue to be examined for producing a radiation-derived image on a mammographic medium, activating an X-ray emanating source to generate a beam of radiant energy, directing the beam of radiant energy to impinge on the tissue-carried tab, on the test material of the tab, on the tissue to be examined, and on radiation-sensitive radiographic recording medium, simultaneously exposing the test material, the tissue and the recording medium to the radiant energy for generating a latent image of the irradiated tissue and of the irradiated test material of the tab, and processing the exposed radiographic recording medium to provide a visually perceptible image indicative of irradiation impedance characteristics of the tissue in an areal field of exposure of the tissue and simultaneously to provide a qualitative radiological visual reference representation of the test material of the tab, providing a tab-carried distribution of particles including particles of one size for use in evaluation of resolution characteristics as well as contrast, and particles of a large size for use in evaluation of contrast characteristics of the generated mammographic film, said method establishing objective and reliable indicia of the quality of a mammogram derived from a diagnostic mammographic procedure carried out.

3. The method as set forth in claim 2 wherein the tab-carried particles are of a nominal diameter of 0.1–0.2 millimeter zinc telluride particles and 0.4–0.5 millimeter rock salt particles.

4. The method as set forth in claim 2 and further comprising the step of limiting the zone containing the test material to an areal expanse corresponding to the area of a circle of about 4.0 millimeters in diameter.

5. A test standard for mammographic X-ray films for facilitating reliable evaluations of film quality characterizing parameters including resolution and contrast in a diagnostic radiograph generated in carrying out a mammographic X-ray procedure.

said test standard comprising:

selectable particulate test material to be exposed to X-ray irradiation during radiographic examination of breast tissue, carrier means supporting said test material as a distribution on said tissue, said carrier means together with said test material being positionable on the breast surface during a radiographic examination of the breast, said test material including particle means whose X-ray image is used for determining the quality of the X-ray film in visually evaluating resolution quality, as well as contrast in a generated radiograph.

6. A test standard for mammographic X-ray films for facilitating reliable evaluations of film quality characterizing parameters including resolution and contrast in a diagnostic radiograph generated in carrying out a mammographic X-ray procedure, said test standard comprising:

selectable particulate test material to be exposed to X-ray irradiation during radiographic examination of breast tissue, carrier means supporting said test material as a distribution on said tissue, said carrier means together with said test material being positionable on the breast surface during examination of the breast radiographically, said test material including particle means, whose X-ray image is used for determining the quality of the X-ray film, and said test material is used for far visually evaluating resolution quality, as well as contrast in a generated radiograph, said test material including zinc telluride particles and rock salt particles.

7. A test standard as set forth in claim 6 wherein said zinc telluride particles are nominally of a size of 0.1–0.2 millimeter in diameter and said rock salt particles are nominally of a size of 0.4–0.5 millimeter in diameter 8. A test standard for mammographic X-ray films for use in reliably evaluating film quality characterizing parameters including resolution and contrast in a diagnostic film generated in carrying out a mammographic X-ray procedure, said test standard comprising:

selectable, test material composed of particles, whose X-ray image is used for determining the quality of the X-ray film when said test material is exposed to X-ray irradiation during radiographic examination of breast tissue, carrier means supporting said test material as a distribution on said tissue, said carrier means together with said test material being positionable on the breast surface during examination of the breast radiographically, said test material being effective to produce on a mammographic film visually perceptible images indicating the quality and the reliability of a mammogram generated in conducting a mammographic examination.

9. A test standard for mammographic X-ray films for use in reliably evaluating film quality characterizing parameters including resolution and contrast in a diagnostic film generated in carrying out a mammographic X-ray procedure, said test standard comprising:

selectable, particulate test material to be exposed to X-ray irradiation during radiographic examination of breast tissue, carrier means supporting said test material as a distribution of said tissue, said carrier means together with said test material being positionable on the breast surface during examination of the breast radiographically, said test material including first particle means of one size for use in visually evaluating resolution quality as well as contrast, and second particle means of a different size for use in visually evaluating contrast quality in a film generated in carrying out a diagnostic mammographic X-ray procedure, said test material being effective to produce on a mammographic film visually perceptible images indicating the quality and the reliability of a mammogram generated in conducting a mammographic examination.

10. A test standard as set forth in claim 9 wherein said test material includes particles opaque to X-ray irradiation for producing on a mammographic film images which visually simulate small particles of calcium of a type which may occur, in human breast tissue, as a sign of cancer.

11. A test standard as set forth in claim 9 wherein said test material includes zinc telluride particles and rock salt particles.

12. A test standard as set forth in claim 11 wherein said zinc telluride particles are nominally of a size of 0.1–0.2 in diameter millimeter and said rock salt particles are nominally of a size of 0.4–0.5 millimeter in diameter.

13. A test standard as set forth in claim 9 and further comprising demarcation means defining boundaries on said carrier means and framing said test material carried thereon for visibly identifying and delineating a quality test reference zone in an X-ray film produced during a diagnostic mammographic procedure.

14. A test standard as set forth in claim 9 wherein said carrier means comprises a band transparent to X-ray irradiation, and further comprising pressure-sensitive adhesive means for securing said band to body tissue.

15. An apparatus for medical use during the conducting of a radiographic examination of the human breast for providing in an exposed radiograph a visual indication of the technical quality and of the reliability of a mammogram for diagnostic use, the radiograph being generated during the examination of the breast, said apparatus comprising a carrier tab including panel means transparent to X-ray irradiation energy and having an areal surface for carrying particles distributed thereon, a plurality of test particles opaque to X-ray irradiation impinging thereupon, whose X-ray image is used for determining the quality of the radiograph, bonding means for holding said test particles affixed on said panel means distributed on said surface thereof, said panel means and said particles distributed thereon being positionable on a selectable surface area of a human breast correlated with a spatial zone thereof to be exposed to X-ray irradiation in conducting a mammographic examination of breast tissue, so that radiographic exposure of said breast tissue and of said particles occur simultaneously during examination to provide radiographic images of the breast tissue and of said particles on said X-ray radiograph.

16. An apparatus for medical use during the conducting of a radiographic examination of the human breast for providing in an exposed radiograph a visual indication of the technical quality and of the reliability of a mammogram for diagnostic use, the radiograph being generated during the examination of the breast, said apparatus comprising a carrier tab including panel means transparent to X-ray irradiation energy and having an areal surface for carrying particles distributed thereon, a plurality of test particles opaque to X-ray irradiation impinging thereupon, said test particles including particles for imaging radiographically to enable evaluation of resolution characteristics of the radiographic image carried on the film, and to enable one to judge contrast quality of the radiograph generated in the mammographic procedure, and said test particles including particles of two distinct sizes including smaller particles for evaluation of resolution quality as well as contrast, and larger particles primarily for evaluation of film image contrast quality, bonding means for holding said test particles affixed on said panel means distributed on said surface thereof, said panel means and said particles distributed thereon being positionable on a selectable surface area of a human breast correlated with a spatial zone thereof to be exposed to X-ray irradiation in conducting a mammographic examination of breast tissue, radiographic exposure of said breast tissue and of said particles occurring simultaneously during examination to provide radiographic images of the breast tissue and of said particles on said X-ray radiograph.

17. An apparatus as set forth in claim 16 and further comprising attachment means for affixing said tab on a human breast to overlie the breast in a zone thereof to be subjected to X-ray examination and for supporting said particles for producing on a radiograph exposed during the conducting of a mammographic examination an image of said particles, said image being generated during radiological examination of the breast.

18. The apparatus as set forth in claim 16 and including zinc telluride particles having a mean diameter of about 0.1–0.2 millimeter for providing a visual indication of resolution quality of the radiographic image as well as contrast, and rock salt particles having a mean diameter of about 0.4–0.5 millimeter for providing a visual indication of contrast quality of the image.

19. The apparatus as set forth in claim 18 and further comprising framing means opaque to X-ray irradiation, and means securing said framing means for delineating a spatial zone in which said particles reside and for facilitating visually locating and identifying a radiograph-quality-indicating test area on the mammogram.

20. The apparatus as set forth in claim 19 wherein said framing means comprise strands of metallic wire arranged perimetrically about said particles.

21. In medical testing to determine possible presence of breast cancer and possible presence of a tissue condition which may be precursory to breast cancer, said testing including the steps of conducting radiographic examination of the breast utilizing x-ray mommography techniques and subsequently diagnostically reviewing resulting mammograms generated, the improvement comprising the step of positioning on and in contact with and overlying the breast during exposure thereof to a radiographic X-ray beam a reference test standard including selectable particulate matter for providing, upon exposure to an X-ray source, a quality indicating test image in the mammogram, said particulate matter including selectable smaller particles providing a test image for use in evaluating resolution and contrast quality of the film, and selectable larger particles for providing a test image for use primarily in evaluating contrast quality of the film, said image being correlated with the technical quality and the diagnostic merit of the visual tissue image depicted on the mammogram to be examined.

* * * * *

UNITED STATES PATENT AND TRADEMARK OFFICE
CERTIFICATE OF CORRECTION

PATENT NO.   :   4,759,045                    Page 1 of 3

DATED        :   July 19, 1988

INVENTOR(S)  :   Harold J. Lasky

It is certified that error appears in the above-identified patent and that said Letters Patent is hereby corrected as shown below:

The Title Page should be deleted to appear as per attached Title Page.

The sheets of drawings of drawing should be deleted to and the attached sheet substituted therefor.

Signed and Sealed this

Thirteenth Day of December, 1988

*Attest:*

DONALD J. QUIGG

*Attesting Officer*     Commissioner of Patents and Trademarks

United States Patent [19]
Lasky

[11] Patent Number: 4,759,045
[45] Date of Patent: Jul. 19, 1988

[54] QUALITY TEST STANDARD FOR X-RAY MAMMOGRAMS

[76] Inventor: Harold J. Lasky, 716 Roslyn Pl., Evanston, Ill. 60201

[21] Appl. No.: 916,162

[22] Filed: Oct. 7, 1986

[51] Int. Cl.⁴ .................................... A61B 6/04
[52] U.S. Cl. ............................ 378/37; 378/162; 378/207
[58] Field of Search ............ 378/18, 37, 162, 165, 378/204, 207, 210; 250/252.1

[56] References Cited

U.S. PATENT DOCUMENTS

| | | | |
|---|---|---|---|
| 2,439,374 | 4/1948 | Leader et al. | 378/165 |
| 3,578,971 | 5/1971 | Lasky | 378/37 |
| 4,506,676 | 3/1985 | Duska | 378/162 |

FOREIGN PATENT DOCUMENTS 3045186 9/1981 Fed. Rep. of Germany ...... 378/204

OTHER PUBLICATIONS

"Roentgenography of the Breast" by Kremins American Jour. of Roentgenology & Nuclear Medicine, vol. 80, #6, Dec. 1958.

Primary Examiner—Craig E. Church
Assistant Examiner—John C. Freeman
Attorney, Agent, or Firm—Michael G. Berkman

[57] ABSTRACT

A method and apparatus for simply, rapidly and reliably determining the diagnostically relevant quality and the general reliability of X-ray mammograms. A mammogram quality reference test standard is provided in which particulate matter of selectable form, composition and size is temporarily affixed on the breast itself for exposure to radiation during production of a diagnostic mammographic radiograph. In a preferred embodiment of the invention, the test standard utilizes particulate matter which includes smaller particles useful in evaluating resolution in the film as well as contrast, and larger particles useful primarily in evaluating contrast in the film. The test zone itself is clearly delineated by suitable, easily visible markers so as clearly to be identifiable, and the area occupied by the test standard is preferably kept small so as to ensure a minimum of interference with a viewing of the image of the tissues of the breast.

21 Claims, 1 Drawing Sheet